United States Patent
Ruddle

(10) Patent No.: US 6,179,617 B1
(45) Date of Patent: Jan. 30, 2001

(54) MICROBRUSH FOR ENDODONTIC USE

(76) Inventor: Clifford J. Ruddle, 227 Las Alturas Rd., Santa Barbara, CA (US) 93103

(*) Notice: Under 35 U.S.C. 154(b), the term of this patent shall be extended for 0 days.

(21) Appl. No.: 09/190,959

(22) Filed: Nov. 12, 1998

(51) Int. Cl.$^7$ .................................................. A61C 5/02
(52) U.S. Cl. ...................................... 433/224; 433/102
(58) Field of Search ..................................... 433/102, 224

(56) References Cited

U.S. PATENT DOCUMENTS 717,594 * 1/1903 Miles, Jr. ............................. 433/102
5,899,693 * 5/1999 Himeno et al. ...................... 433/119

OTHER PUBLICATIONS

D. Keir et al., "Effectiveness Of A Brush In Removing Postinstrumentation Canal Debris" pp. 323–327, Journal Of Endodontics, vol. 16, No. 7 (Jul. 1990).

* cited by examiner

Primary Examiner—John J. Wilson
(74) Attorney, Agent, or Firm—Polster, Lieder, Woodruff & Lucchesi

(57) ABSTRACT

A micro-brush is provided to remove the smear layer that remains in the root canal after the pulp, bacteria, and related irritants have been mechanically and chemically removed from the root canal using files and sodium hypochlorite. The brush includes a shaft or shank and a tapered brush section extending from the distal end of the shank. The brush section includes a plurality of bristles extending radially from a central wire base. The bristles can be formed in a reverse thread pattern. The shank can be provided with a handle for manual use or the shank can be adapted to be received in a rotary, sonic, or ultrasonic handpiece to impart rotational or vibratory motion to the micro-brush. The brush section has a diameter of between about 0.2 mm and about 0.7 mm at a tip end and a diameter of between about 1 mm and 2 mm at a coronal-most end. The brush section is about 16 mm long, and thus has a taper of about 0.06 mm/mm and about 0.12 mm/mm.

16 Claims, 1 Drawing Sheet

MICROBRUSH FOR ENDODONTIC USE

CROSS-REFERENCE TO RELATED APPLICATIONS

Not Applicable

STATEMENT REGARDING FEDERALLY SPONSORED RESEARCH OR DEVELOPMENT

Not Applicable.

BACKGROUND OF THE INVENTION

This invention relates to microbrushes, and, in particular, to brushes which are used during an endodontic or root canal procedure to more predictably clean the root canal system prior to obturation.

Following tooth maturation, the dental pulp is harbored within the structural elements of the tooth. Frequently, and for a variety of reasons, the pulp is irreversibly injured, resulting in inflammatory and infectious conditions which often adversely affect the tooth, its supporting structures, and the patient's health. Clinically, as an alternative to extraction, root canal treatment is performed and ideally directed towards the elimination of pulp, bacteria, and related irritants from the root canal system, followed by three-dimensionally filling the root canal space with an inert, biocompatible, dimensionally stable, filling material, such as gutta percha. The obturation procedures will fill not just the main canal, but the fins, webs, cul-de-sacs, lateral canals, and all portals of exit between the root canal system and the tooth's attachment apparatus.

Root canal procedures are common. In 1994 alone, some 40 million root canal procedures were performed in the United States. Central to a successful endodontic treatment has been the use of chemicals to enhance canal debridement during cleaning and shaping procedures to facilitate the preparation and complete cleaning of the root canal system. The chemicals used to enhance canal debridement during cleaning and shaping procedures potentially reach all aspects of the root canal system. The most popular chemicals currently used during canal preparation to actively assist in cleaning include bleach, hydrogen peroxide, and chelating agents. Often, a 2%–5% solution of a clear, pale, greenish-yellow strongly alkaline solution of sodium hypochlorite (NaOCl) is used.

During canal preparation, the sodium hypochlorite solution is liberally irrigated into the root canal space where its solvent action facilitates the digestion and removal of pulp and bacteria and the destruction and removal of viruses, spores, endotoxins and other irritants generated by the microorganisms in the canal system as the solution penetrates into all aspects of the root canal system. However, studies have shown that even the most thorough use of sodium hypochlorite does not remove all the material from the root canals. The root canals are defined by millions of dentinal tubules per square millimeter, and the irritants can find their way into the tubules of the root canal systems. Thus, after cleaning and shaping procedures, the root canal is still covered with a film of debris, frequently described in the literature as a "smear layer." This "smear layer" includes dentinal mud and/or organic debris, including the irritants noted above.

The smear layer or film compromises the sealing of the root canal system with gutta percha and root canal sealer. If obturation is incomplete then the root canal space is predisposed to leakage and failure. Post-treatment failures attributable to leakage are common and require endodontic retreatment of the tooth. Thus, for a complete and thorough cleaning, this smear layer or film should be removed. Once the existence of this smear layer was discovered, practitioners began using a weak acid or surfactant, such as 17% EDTA ethyldiamine-tetraacetic acid), in an effort to remove the smear layer. Typically, the root canal is flushed with EDTA to accomplish this. Some practitioners have been known to use root canal instruments or files to enhance the performance of the EDTA. The files may be manually used or may be mounted in a rotary or vibratory handpiece. Even when files are used, it is difficult to ensure that the file is brought into contact with the complete surface of the root canal, and hence it is difficult to ensure that substantially all of the smear layer has been removed. Additionally, the use of files, especially with a handpiece, leads to iatrogenic events, such as broken instruments, ledges in the wall of the root canal preparaion, or even perforation of the root canal system. Thus, it is desirable to provide a tool which can remove the smear layer without the associated possibility of iatrogenic events associated with the use of files and other hard instruments.

BRIEF SUMMARY OF THE INVENTION

Briefly stated, a micro-brush is provided which can be used to reach into the root canal to brush and make intimate contact with normal root canal irregularities that exist even after optimal canal preparation procedures. This brushing action facilitates removing the smear layer which remains in the root canal after the pulp and irritants have been mechanically and chemically removed from the root canal using files and sodium hypochlorite. The brush is used in association with an intracanal irrigant such as EDTA, to remove the debris or smear layer or film, from the root canal.

The brush includes a shaft or shank and a tapered brush section depending from the shank. The brush section includes a plurality of bristles extending radially from a central wire base. The bristles are made from a material which is sufficiently stiff so that it will have good rubbing action against the root canal wall to remove the smear layer, which is sufficiently pliable so that it can bend and flex to reach the normal irregularities in the root canal wall, and which is sufficiently soft so that the use of the brush will not form gouges or ledges in the root canal wall (i.e., will not substantially change the normal morphology of the root canal system). The bristles can be formed in a reverse thread pattern so that rotation of the brush in the root canal will pull the contents of the smear layer coronally. The shank can be provided with a handle for manual use or can be adapted to be received in a rotary or vibratory (sonic and ultrasonic) handpieces to impart rotational or vibratory motion to the micro-brush.

The brush section has a diameter of between about 0.2 mm and about 0.5 mm at a tip end and a diameter of between about 1 mm and 2 mm at its coronal end. The brush section is about 16 mm long, and thus has a taper of between about 0.06 mm/mm and about 0.12 mm/mm.

A finishing technique that enhances the cleanliness of a root canal preparation utilized before packing or obturation procedures during an endodontic procedure on a living patient includes the steps of preparing an access cavity to expose the orifice(s) to the root canal beneath the pulp chamber of the tooth crown; mechanically preparing and chemically eliminating the soft tissue, bacteria, and related irritants from the root canal system; flushing the root canal after it has been debrided with a chelating agent; and agitating the chelating agent in the root canal with the brush.

BRIEF DESCRIPTION OF THE SEVERAL VIEWS OF THE DRAWINGS

Corresponding reference numerals will be used throughout the several figures of the drawings.

DETAILED DESCRIPTION OF THE INVENTION

Figure 1:
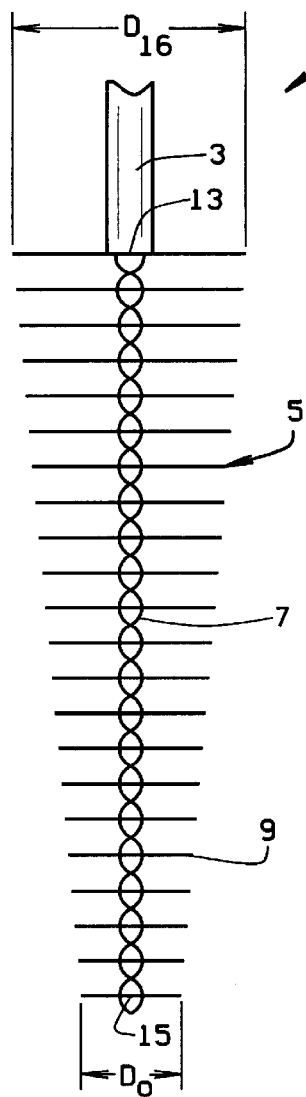
FIG. 1 is a schematic side elevational view of a brush of the present invention.

The following detailed description illustrates the invention by way of example and not by way of limitation. This description will clearly enable one skilled in the art to make and use the invention, including what I presently believe is the best mode of carrying out the invention. "Dentist" or "practitioner" is used broadly herein to include all those who perform dental work, and is intended to include, for example, general dentists and specialists within the various fields of dentistry, such as oral surgeons, endodontists, periodontists, prosthodontists, and pedodontists, etc.

As noted above, after a practitioner cleans and shapes a patient's root canal during an endodontic procedure, the practitioner floods the root canal with EDTA to remove the smear layer from the root canal. To facilitate removal of the film or smear layer, a brush 1 of the present invention is used. The brush 1 includes a shaft or shank section 3 and a brush section The brush section preferably is about 16 mm long. The shank section 3 is about 5–9 mm long to give the brush 1 an overall length of about 21–25 mm. If desired, the shank could be made longer.

The brush section 5 includes a braided or twisted wire base 7 which is fixed to the distal end of the shank 3. A plurality of bristles 9 radiate from the wire base 7 to define the brush section 5. The bristles are made from a material which is sufficiently stiff so that the bristles will have good rubbing action against the root canal wall so that substantially all of the smear layer will be removed during use of the brush. The material is sufficiently pliable so that it can bend and flex to reach the normal irregularities in the root canal wall. Further, the material cannot be so stiff that it will create gouges or ledges in the root canal system, or otherwise substantially change the normal morphology or anatomy of the root canal system. Additionally, the bristle material must be durable, so that it will function properly to remove the smear layer. If the microbrush is not durable, the bristles could dislocate or fray at their ends, and become ineffective in removing the smear layer from the root canal. Preferably, the bristles are nylon. However, other materials could also be used. The bristles are populated densely enough so that the bristles will be able to brush substantially all of the root canal surface to ensure that substantially all of the smear layer will be removed.

The diameter of the brush section 5 is tapered, from a small diameter $D_o$ at its tip 15 to a larger diameter $D_{16}$ at its coronal end 13. Preferably, the taper is gradual. The brush is preferably available in four sizes: fine, fine-medium, medium, and medium-large, to cover variations in the diameter of the canals following root canal preparation procedures. Thus, for example, the fine brush can have a tip diameter at $D_o$ of about 0.2 mm and a coronal end diameter at $D_{16}$ of about 1 mm; the fine-medium brush can have a tip diameter at $D_o$ of about 0.35 mm and a coronal end diameter at $D_{16}$ of about 1.25 mm; the medium brush can have a tip diameter at $D_o$ of about 0.5 mm and a coronal end diameter at $D_{16}$ of about 1.5 mm; and the medium-large brush can have tip diameter at $D_0$ of about 0.7 mm and a coronal end diameter at $D_{16}$ of about 2.0 mm. Thus, the slope of the taper is between about 0.06 mm/mm to about 0.12 mm/mm.

Figure 2:
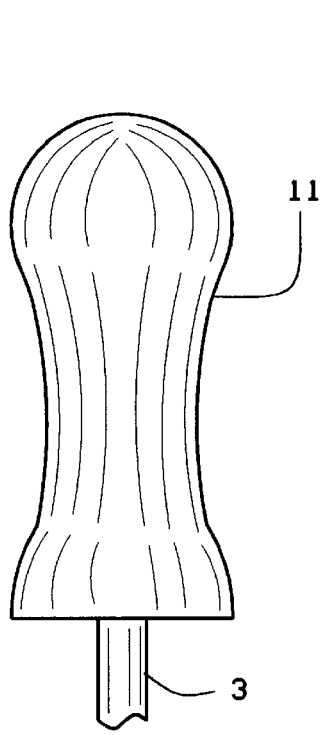
FIG. 2 is a side elevational view of the shaft or shank of the brush provided with a handle to facilitate manual use of the brush.
Figure 3:
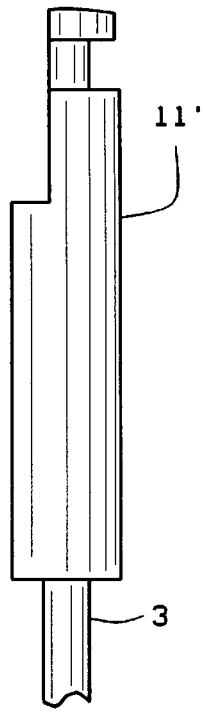
FIG. 3 is an elevational view of the shaft or shank of the brush, adapted for use with a rotational handpiece.
Figure 4:
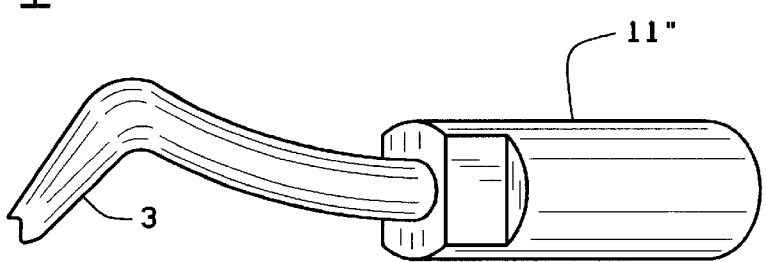
FIG. 4 is a view of the shaft or shank of the brush, adapted for use with an ultrasonic handpiece.

The shaft 3 can be provided with a handle 11, such as shown in FIG. 2 so that the brush can be easily grasped and manipulated by a practitioner. Alternately, the shaft 3 can be adapted so that the brush can be inserted in a handpiece which will impart either rotational motion or vibratory motion to the brush. In FIG. 3, the shaft 3 is shown to have latch-type end 11' to enable the it to be received in a slow speed handpiece which operates at about 150–300 rpm's. The handpiece, when operated, will rotate the brush within the root canal. Additionally, the brush 1 can be received in a vibratory handpiece, such as a sonic, ultrasonic, or piezoelectric handpiece, for example, which will impart vibratory motion to the brush. In this instance, the end of the shaft 3 extends from an end 11" which is threaded at its proximal end to enable the brush to be mounted to an ultrasonic handpiece, in a conventional manner.

Use of the brush with either a rotational or vibratory handpiece will enable the practitioner to provide a constant, even motion of the bristles in the root canal to make intimate contact of the brush bristles against the irregularities normally occurring in the prepared root canal wall to remove the smear layer from the canal. The motion of the brush within the root canal would also agitate the EDTA within the root canal to enhance the ability of the EDTA to remove substantially all of the smear layer from the root canal wall and enhance its ability to penetrate into all aspects of the root canal system.

The bristles 9 can be mounted to the wires 7 to have a reverse thread. Thus, while the brush 1 is being rotated in the root canal, the thread pattern of the bristles will pull the components of the smear layer out of the root canal rather than pushing or urging the contents of the smear layer towards the apex of the root canal.

Gutta percha master cones utilized to obturate root canal systems are available in a variety of sizes, but typically sizes fine, fine-medium, medium, and medium-large are selected. These master cones are typically conical in shape, terminating at a point at their most distal ends. In use, a cone is selected whose rate of taper is less than the rate of taper of the root canal. Additionally, the tip of the master cone is cut off at a desired point by the practitioner so that its apical cross-sectional diameter corresponds closely to the apical diameter of the canal to be filled. The master cone is then buttered with a root canal sealer and inserted into the root canal. Gutta percha when thermally softened is pliable and moldable, and a prefit plugger can adapt this material to the shape of the root canal generating enormous sealer hydraulics which force the sealer into the dentinal tubules, thereby three-dimensionally filling and sealing the canal. The gutta percha master cone chosen by the practitioner depends on the size of the canal to be packed. The brush sizes correspond generally to the sizes of gutta percha master cones commonly used in practice, and the brush used by the practitioner will correspond generally to the size of the gutta percha master cone selected. Thus, if a fine-medium gutta percha master cone is selected, a fine-medium brush will be used. Similarly, if a medium-large gutta percha master cone is selected, a mediumlarge brush will be used. The contact of the micro-brush with the root canal, as noted above, will enhance removal of the smear layer film from the irregularly shaped root canal system. Because the brush corresponds generally in size and shape to the gutta percha cone selected, the internal walls of the root canal system will be additionally cleansed as the bristles of the brush will easily adapt and conform to the root canal anatomy, and contact substantially all of the root canal wall. Enhanced cleaning of the root canal system will provide a better seal between the gutta percha/sealer combination and the root canal anatomy.

In view of the above, it will be seen that the several objects and advantages of the present invention have been achieved and other advantageous results have been obtained. As various changes could be made in the above constructions without departing from the scope of the invention, it is intended that all matter contained in the above description or shown in the accompanying drawings shall be interpreted as illustrative and not in a limiting sense. For example, although the brush is shown to be adapted for use with either rotational or vibratory handpieces (in addition to manual use) the brush can be adapted for use with other types of handpieces. Additionally, the brush can be adapted for use with other types of vibratory handpieces in addition to the sonic and ultrasonic handpieces currently known. The length and taper of the brush section can be altered if desired, to make either a shorter or a longer brush section, or a smaller or greater taper, or a parallel walled or cylindrical brush. Although described primarily for use with human patients, it will be evident that the brush can be used in endodontic procedures performed on animals. These examples are merely illustrative.

What is claimed is:

1. A brush for use in cleaning a root canal during an endodontic procedure on a living patient after the root canal has been shaped but before obturation of the root canal system; the brush having a shank and a brush section extending from the shank; the brush section including a central core extending from the shank and a plurality of bristles radiating from the central core, the brush section being tapered, the taper of the brush being between about 0.06 mm/mm and about 0.12 mm/mm and the bristles defining a reverse thread pattern.

2. The brush of claim 1 wherein the shank is adapted to be mounted to a handpiece.

3. The brush of claim 2 wherein the shank is adapted to be mounted to a rotary handpiece.

4. The brush of claim 3 wherein the shank is adapted to be mounted to a vibratory handpiece.

5. The brush of claim 1 wherein the brush section has a diameter of between about 0.2 mm and about 0.7 mm at a tip end and a diameter of between about 1 mm and 2 mm at its coronal end.

6. The brush of claim 1 wherein the brush has a diameter of between 0.2 mm and 0.5 mm at its tip end.

7. The brush of claim 1 wherein the brush has a diameter of between 1 mm and 2 mm at its coronal end.

8. A method of enhanced cleaning of a root canal system for obturation during an endodontic procedure on a tooth of a living patient; the method comprising;
preparing an access cavity in the patient's tooth;
exposing the orifice(s) of the root canal system beneath the pulp chamber of the tooth;
mechanically and chemically removing the, soft tissue from the root canal to debride the root canal;
flushing the root canal system after it has been debrided with a chelating agent; and
agitating the chelating agent in the root canal system with a brush; the brush having a shank and a tapered brush section extending from the shank; the brush section including a plurality of bristles.

9. The method of claim 8 wherein the shank is adapted to be received in a sonic or ultrasonic handpiece; the agitating step including vibrating the brush within the root canal.

10. The method of claim 8 wherein the shank is adapted to be received in a rotary handpiece; the agitating step including rotating the brush within the root canal.

11. The method of claim 10 wherein the bristles define a reverse thread pattern, whereby the rotation of the brush within the root canal pulls soft material and debris out of the canal.

12. A brush for use in cleaning a root canal during an endodontic procedure on a living patient after the root canal has been shaped but before obturation of the root canal system; the brush having a shank and a brush section extending from the shank; the brush section including a central core extending from the shank and a plurality of pliable bristles radiating from the central core, the bristles being sized to reach the normal irregularities in the root canal wall and being sufficiently stiff so that the bristles will remove a smear layer and other debris from the root canal wall as the bristles are moved against the root canal wall; the bristles defining a reverse thread pattern.

13. The brush of claim 12 wherein the brush section is tapered, the taper of the brush being between about 0.06 mm/mm and about 0.12 mm/mm.

14. A brush for use in cleaning a root canal during an endodontic procedure on a living patient after the root canal has been shaped but before obturation of the root canal system; the brush having a shank and a brush section extending from the shank; the brush section including a central core extending from the shank and a plurality of bristles radiating from the central core, the brush having a tip end and a coronal end, the brush having a diameter of less than 0.7 mm at its tip end, said bristles defining a reverse thread pattern.

15. The brush of claim 14 wherein the brush section is tapered, the taper being between about 0.06 mm/mm and about 0.12 mm/mm.

16. The brush of claim 14 wherein the brush has a diameter of between about 1 mm and about 2 mm at its coronal end.

* * * * *